(12) United States Patent
Mittal et al.

(10) Patent No.: US 10,485,517 B2
(45) Date of Patent: Nov. 26, 2019

(54) COMPUTATIONAL FLOW DYNAMICS BASED METHOD FOR ESTIMATING THROMBOEMBOLIC RISK IN PATIENTS WITH MYOCARDIAL INFARCTION

(71) Applicant: THE JOHNS HOPKINS UNIVERSITY, Baltimore, MD (US)

(72) Inventors: Rajat Mittal, Vienna, VA (US); Richard Thomas George, Sparks, MD (US); Jung Hee Seo, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 983 days.

(21) Appl. No.: 14/767,668

(22) PCT Filed: Feb. 17, 2014

(86) PCT No.: PCT/US2014/016683
§ 371 (c)(1),
(2) Date: Aug. 13, 2015

(87) PCT Pub. No.: WO2014/127320
PCT Pub. Date: Aug. 21, 2014

(65) Prior Publication Data
US 2016/0004837 A1    Jan. 7, 2016

Related U.S. Application Data

(60) Provisional application No. 61/765,235, filed on Feb. 15, 2013.

(51) Int. Cl.
*A61B 8/08* (2006.01)
*A61B 5/00* (2006.01)
(Continued)

(52) U.S. Cl.
CPC .......... *A61B 8/5261* (2013.01); *A61B 5/0035* (2013.01); *A61B 5/0044* (2013.01);
(Continued)

(58) Field of Classification Search
CPC ... A61B 5/0402; A61B 5/0044; A61B 5/7275; A61B 5/0035; A61B 5/055; A61B 8/5261; A61B 8/488; A61B 8/06; A61B 6/503; A61B 6/032; A61B 6/5247; G16H 50/30; G16H 50/50; G06F 19/3431
See application file for complete search history.

(56) References Cited

U.S. PATENT DOCUMENTS

2007/0116335 A1* 5/2007 Capolunghi ............. G06T 7/12
                                                       382/128
2010/0074494 A1   3/2010 Karmonik et al.
(Continued)

OTHER PUBLICATIONS

Cheek, Carlos, "Evaluation of a numerical thrombosis model for a high shear rotating flow" (2008). Thesis. Rochester Institute of Technology. Accessed from.*
(Continued)

*Primary Examiner* — Bo Joseph Peng
(74) *Attorney, Agent, or Firm* — MH2 Technology Law Group LLP (57) ABSTRACT

The present invention provides a method for determining thromboembolic risk in a patient. The method includes processing functional images of a patient's heart in order to create a computational fluid dynamic (CFD) modeling of the patient's heart. Once a CFD model is obtained, various metrics can be determined to estimate the patient's risk of left ventricular thrombosis. This method is particularly suited for determining thromboembolic risk in patients having suffered a myocardial infarction. However, the method can also be applied to a broader population at risk of cardioembolic and cryptogenic stroke.

20 Claims, 9 Drawing Sheets (51) Int. Cl.
*A61B 5/055* (2006.01)
*A61B 6/03* (2006.01)
*A61B 6/00* (2006.01)
*A61B 8/06* (2006.01)
*G16H 50/30* (2018.01)
*G16H 50/50* (2018.01)
*A61B 5/0402* (2006.01)

(52) U.S. Cl.
CPC ............ *A61B 5/055* (2013.01); *A61B 5/7275* (2013.01); *A61B 6/032* (2013.01); *A61B 6/503* (2013.01); *A61B 6/5247* (2013.01); *A61B 8/06* (2013.01); *A61B 8/488* (2013.01); *G16H 50/30* (2018.01); *G16H 50/50* (2018.01); *A61B 5/0402* (2013.01)

(56) References Cited

U.S. PATENT DOCUMENTS

| | | |
|---|---|---|
| 2010/0268070 A1 | 10/2010 | Jaffer et al. |
| 2010/0278405 A1* | 11/2010 | Kakadiaris ............. G06F 19/00 382/131 |
| 2010/0280352 A1* | 11/2010 | Ionasec ................ A61B 5/0263 600/407 |
| 2010/0298719 A1 | 11/2010 | Kock et al. |
| 2011/0060576 A1 | 3/2011 | Sharma et al. |
| 2012/0059246 A1 | 3/2012 | Taylor |
| 2012/0215510 A1 | 8/2012 | Metaxas |
| 2013/0197884 A1* | 8/2013 | Mansi ..................... G06T 19/00 703/2 |

OTHER PUBLICATIONS

Mihalef, V., et al., "Patient-specific modeling of left heart anatomy, dynamics and hemodynamics from high resolution 4D CT", Biomedical Imaging: From Nano to Macro, IEEE International Symposium, pp. 504-507, Apr. 14-17, 2010.

Mihalef, V., et al., "Patient-specific modelling of whole heart anatomy, dynamics and haemodynamics from four-dimensional cardiac CT images", Interface Focus, (2011) vol. 1, pp. 286-296.

* cited by examiner

COMPUTATIONAL FLOW DYNAMICS BASED METHOD FOR ESTIMATING THROMBOEMBOLIC RISK IN PATIENTS WITH MYOCARDIAL INFARCTION

CROSS-REFERENCE TO RELATED APPLICATIONS

This application is a 35 U.S.C. § 371 U.S. national entry of International Application PCT/US2014/016683, having an international filing date of Feb. 17, 2014, which claims the benefit of U.S. Provisional Application No. 61/765,235, filed Feb. 15, 2013, the content of each of the aforementioned applications is herein incorporated by reference in their entirety.

GOVERNMENT SUPPORT

The present invention was made with government support under grant number IOS 1124804 awarded by the National Science Foundation. The government has certain rights in the present invention.

FIELD OF THE INVENTION

The present invention relates generally to cardiac care. More particularly, the present invention relates to a method of assessment and estimation of thromboembolic risk in patients with cardiomyopathy as a result of myocardial infarction, but can also be extended to patients with a non-ischemic cardiomyopathy.

BACKGROUND OF THE INVENTION

Stroke is a major source of morbidity and mortality in the United States with 795,000 strokes per year. Sixty percent of strokes are ischemic in nature and 20% are cardioembolic in origin. Patients with heart failure (HF) and left ventricular (LV) systolic dysfunction have higher rates of thromboembolic events including embolic stroke and peripheral arterial thrombi compared with the general population. It is well known that a common cause of arterial emboli in heart failure patients is myocardial infarction (MI) and subsequent left ventricular (LV) mural thrombus formation. LV thrombus (LVT) formation is initiated by platelet deposition on the endocardial surface of akinetic or dyskinetic myocardium with endothelium that is dysfunctional secondary to an inflammatory response.

In the era prior to reperfusion therapy (thrombolytics and primary percutaneous coronary intervention), the risk of thrombus formation in the setting of an anterior MI was more than 50% according to autopsy and surgical findings. However, reperfusion therapy has demonstrated a reduction in the incidence of LV thrombus to approximately 10% in patients with anterior MI. Most of these thrombi develop within the first two weeks after an acute MI. However, the risk continues to be elevated thereafter. Those patients who develop an LVT are at high risk of an embolic event (odds ratio 5.5, 95% CI 3.0-9.8) compared to those without LVT. This risk is greatest in the first 3-4 months, but continues out to at least 96 months.

Global or regional stagnation of blood and endocardial injury is hypothesized to promote the development of LVT. In particular, studies have shown that the presence of LVT following acute infarction is related to the location and size of infarction and the presence of pump failure. Anterior wall infarctions typically result in a greater area of necrotic myocardium than do infarctions in other areas, and thus adversely affect global LV function to a larger extent. Furthermore, in contrast to inferior wall infarction, apical dyskinesia occurs frequently secondary to anterior wall infarction, and predisposes to regional stasis of blood.

The identification of high risk patients and the pharmacologic prevention of LVT formation is the key to preventing embolic events. Stratification of patients at risk for LVT formation is currently limited, and primarily based on global assessment of ventricular function and image based assessment of ventricular wall motion. Patients are considered high-risk for thromboembolism if they have (a) LVEF<30% and (b) an antero-apical wall motion abnormality or an LV aneurysm on imaging. However, even those patients with an LVEF of 30-40% are still at increased risk. Current guidelines recommend parental anticoagulation with heparin once an "at risk" patient is identified. Heparin has been shown to significantly lower the risk of LV thrombus formation from 32% to 11% in the pre-reperfusion era. Once the aPTT is 2-3 times the control value, oral anticoagulation with warfarin is instituted with a target INR of 2.5 (range: 2.0-3.0) [9]. Warfarin is continued for 3-6 months. The use of warfarin is associated with an 86% reduction in the rate of embolization.

The majority of patients presenting with an acute ST elevation myocardial infarction (STEMI) undergo invasive coronary angiography and implantation of a drug-eluting intracoronary stent. Medical therapy following implantation of a stent requires "dual anti-platelet therapy" using aspirin and clopidogrel or prasugrel for at least one year and often longer. In patients considered at high risk of LVT formation, current guidelines recommend adding heparin and then warfarin to dual-antiplatelet in post-MI patients who have undergone reperfusion therapy with intracoronary stenting. This so called "triple therapy" significantly increases the fatal and non-fatal bleeding risk to 22.6% in the first 30 days and remains above 20% out to 90 days, the window when patients are at highest risk of LV thrombus formation. Current risk stratification methods therefore result in the treatment of 10 patients to prevent LV thrombus in 1 patient while the risk of bleeding is 1 in 5. Clearly, more effective methods of risk stratification are needed.

It would therefore be advantageous to provide a diagnostic method to aid in selecting those patients most likely to benefit from triple therapy or similar therapies designed to reduce thromboembolic risk.

SUMMARY

The foregoing needs are met, to a great extent, by the present invention, wherein in one aspect a method for estimating thromboembolic risk in a patient includes obtaining a high resolution functional image of the heart of the patient and constructing a patient specific model using the image data obtained from the functional image of the heart of the patient. The method also includes modeling computational fluid dynamics (CFD) of the heart of the patient using the patient specific model to obtain fluid dynamics data from the image data. Additionally, the method includes validating the fluid dynamics data against data obtained from an echocardiogram or another imaging modality of the heart of the patient. Calculating thrombogenic metrics from the fluid dynamics data and generating a thrombogenic risk assessment using the metrics are also included in the method.

In accordance with an aspect of the present invention, the method can include obtaining the functional image is done using at least one of a CT scanner, cardiovascular magnetic resonance imager, echocardiography, and radionuclide imaging. The method can also include segmenting the functional image of the heart of the patient to obtain a model of the left ventricle of the heart, registering a template of a generic left ventricle to the model of the left ventricle of the patient, and simulating left ventricle flow for the model of the left ventricle.

In accordance with another aspect of the present invention, the method further includes segmenting the left ventricle model into approximately 20 or more individual phases over one cardiac cycle. Boundaries for a thrombus in the left ventricle model can be identified and resected from the model. The template of the generic left ventricle can also be registered to each of the approximately 20 individual phases. The method can include performing a space-time interpolation to translate each of the approximately 20 registered phases of the template to $O(10^3)$ frames. The thrombogenic metrics can also include at least one selected from a group of particle residence time (PRT), particle travel distance (PTD), mean particle speed (MPS), near-wall particle displacement (NWPD), wall shear stress (WSS), thrombin concentration (TC), activated free platelet concentration (ApPC) or bound platelet concentration (BPC).

In accordance with yet another aspect of the present invention, a non-transitory computer readable medium is programmed with steps including receiving data related to a functional image of a heart of the patient and constructing a patient specific model using the image data obtained from the functional image of the heart of the patient. The non-transitory computer readable medium is also programmed to model computational fluid dynamics (CFD) of the heart of the patient using the patient specific model to obtain fluid dynamics data from the image data and validating the fluid dynamics data against data obtained from an echocardiogram of the heart of the patient. Additionally, the non-transitory computer readable medium is programmed with steps including calculating thrombogenic metrics from the fluid dynamics data and generating a thrombogenic risk assessment using the metrics.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIGS. 5E and 5F further illustrate the typical segmentation of the LV that will be employed.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention provides a method for determining thromboembolic risk in a patient. The method includes processing functional images of a patient's heart in order to create a computational fluid dynamic (CFD) modeling of the patient's heart. Once a CFD model is obtained various metrics can be determined to estimate the patient's risk of left ventricular thrombosis. This method is particularly suited for determining thromboembolic risk in patients having suffered a myocardial infarction, but can also be applied to patients with cardiomyopathy due to other causes. However, the method can also be applied to a broader population at risk of cardioembolic and cryptogenic stroke.

Figure 1:
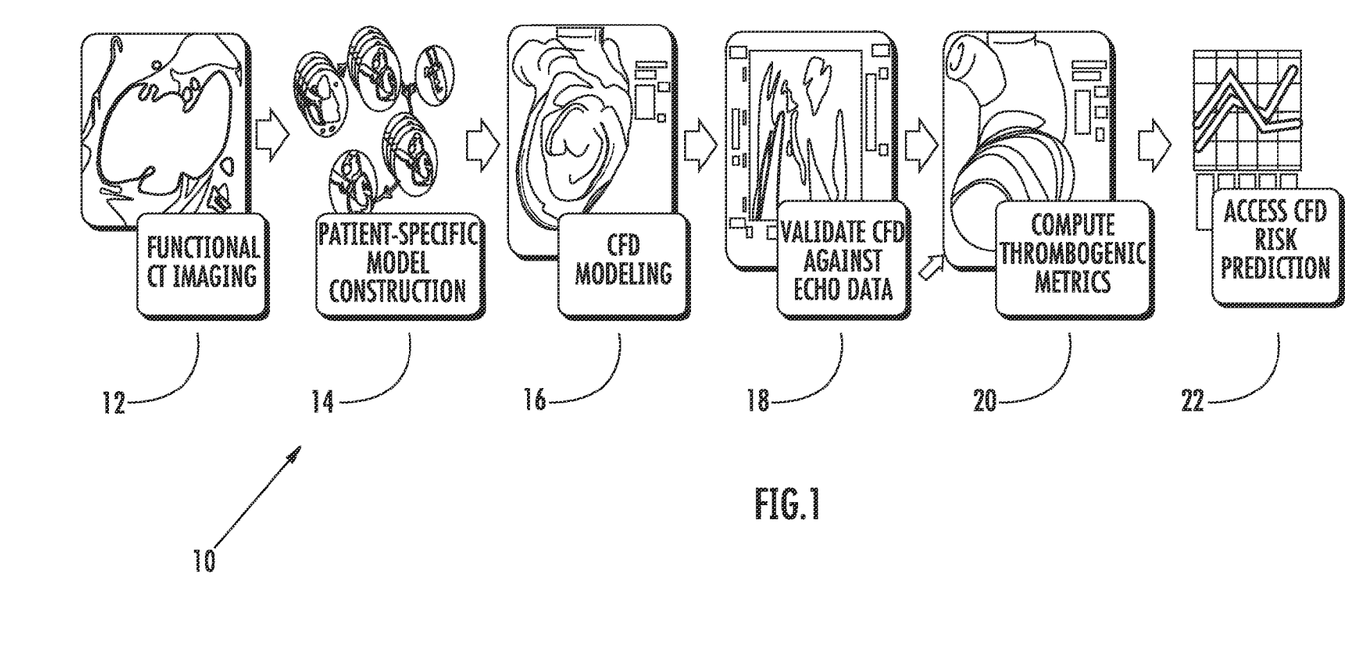
FIG. 1 illustrates a method of estimating thromboembolic risk in a patient having suffered a myocardial infarction, according to an embodiment of the present invention.

FIG. 1 illustrates a method of estimating thromboembolic risk in a patient having suffered a myocardial infarction. The method 10 includes a step 12 of obtaining a functional image of a heart of the patient. The functional image can be obtained using a number of imaging modalities including but not limited to computed tomography scanning, echocardiogram, magnetic resonance imaging, cardiovascular magnetic resonance imager, radionuclide imaging and positron emission tomography. Any combination of these imaging modalities can also be used. In step 14 a patient specific model is constructed using the image data obtained from the functional image of the heart of the patient. The method of constructing the patient specific model will be discussed in further detail with respect to FIG. 2. Computational fluid dynamics (CFD) modeling is done in step 16 to obtain fluid dynamics data from the image data. Step 18 includes validating the fluid dynamics data against data obtained from an echocardiogram of the heart of the patient. Thrombogenic metrics are calculated from the fluid dynamics data in step 20, and step 22 includes generating a thrombogenic risk assessment using the metrics. It should be noted that a computing device configured to execute these steps can be used. The computing device can be hard wired to the imaging machine or can be networked in a wired or wireless manner. The computing device can also communicate with a server or other remote computing device in order to execute these steps. The computing device can take the form of a personal computer, tablet computing device, smart phone, server, processor, imaging device computer, or any other suitable computing device known to or conceivable by one of skill in the art. In addition the method can be programmed onto a non-transitory computer readable medium executable by the computing device. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

Figure 2:
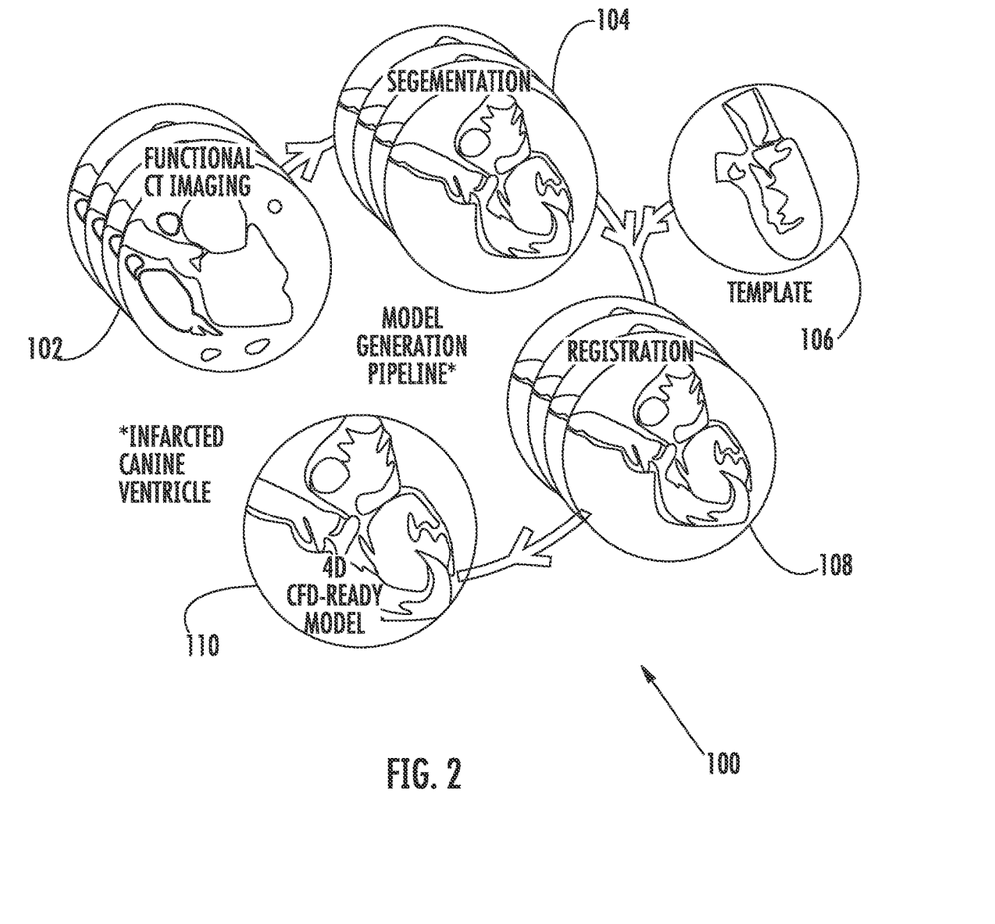
FIG. 2 illustrates a patient specific model, discussed with respect to FIG. 1, according to an embodiment of the present invention.

FIG. 2 further illustrates the patient specific model constructed in step 14, discussed with respect to FIG. 1. As illustrated in FIG. 2, the patient specific model is constructed via the method 100, using data from the functional image of the heart of the patient, in step 102. Preferably, this functional image is obtained with a CT scanner. However, any imaging modality known to or conceivable by one of skill in the art can also be used. Step 104 of the method 100 includes segmenting the functional CT scan of the heart of the patient to obtain a model of the left ventricle of the patient's heart. A template of a generic left ventricle is registered to the model of the left ventricle of the patient in steps 106 and 108. Step 110 includes simulating left ventricle flow for the model of the left ventricle of the patient's heart. This information can then be used according to the method described above with respect to FIG. 1 in order to determine a thrombogenic risk for the patient. It should be noted that a computing device configured to execute these steps can be used. The computing device can be hard wired to the imaging machine or can be networked in a wired or wireless manner. The computing device can also communicate with a server or other remote computing device in order to execute these steps.

The following describes an exemplary implementation of the methods described above with respect to FIGS. 1 and 2. This imaging example is in no way meant to be considered limiting, and any other implementation known to or conceivable by one of skill in the art could also be used. In order to obtain a functional CT-image of the patient's heart, depending on patient size, iodinated contrast (iopamidol, 370 mgI/ml) is infused at a rate of 4-5 ml/sec for a total of 40-60 ml. CT imaging is performed using a 320-row detector system with full cardiac coverage (Aquilion ONE, Toshiba Medical Systems). Imaging is performed over 3 heart beats to achieve a temporal resolution of 58 msec. Alternatively, imaging could be obtained with alternative X-ray CT systems, MR imaging, nuclear imaging, or echocardiography.

Figure 3:
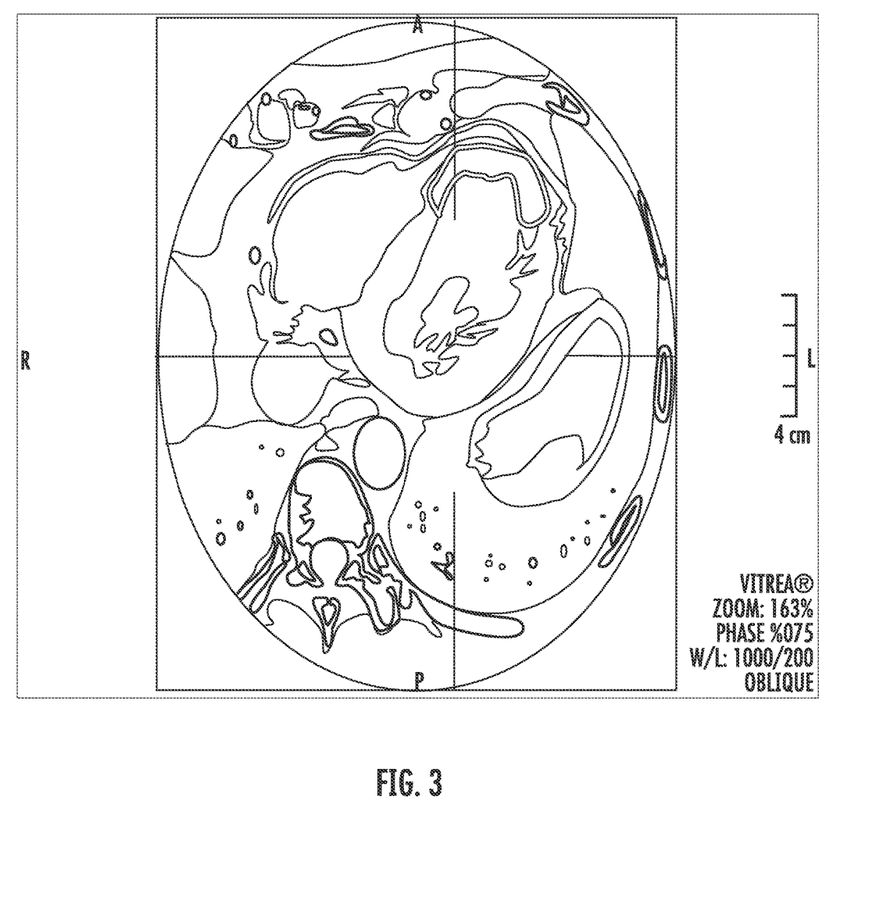
FIG. 3 illustrates identification of a thrombus in a CT image of a left ventricle, according to an embodiment of the present invention.
Figure 4:
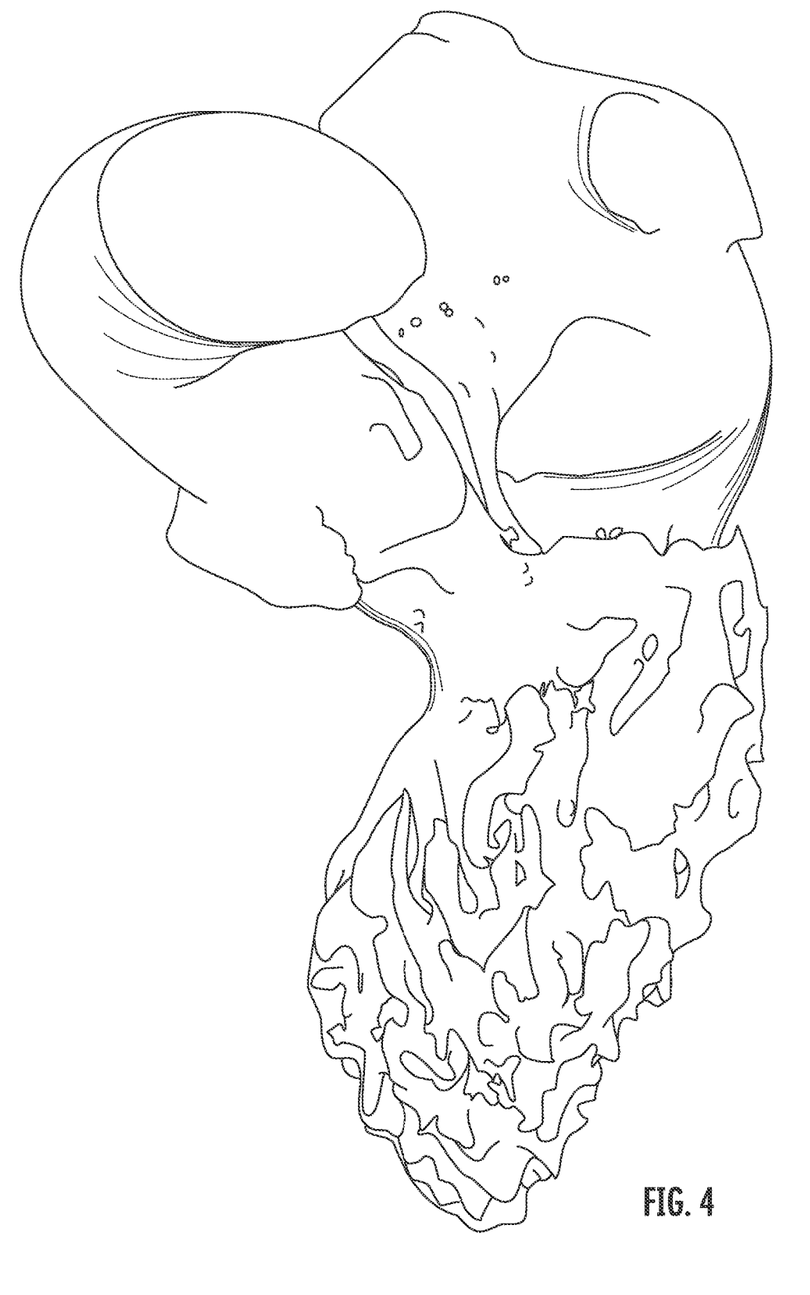
FIG. 4 illustrates segmentation of a left ventricular model from CT data, according to an embodiment of the present invention.
Figure 5A:
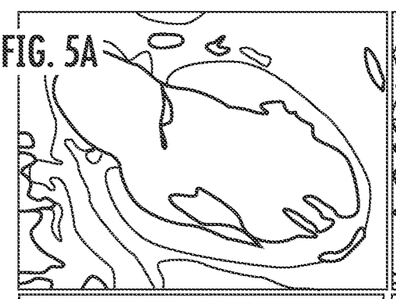
FIGS. 5A, 5B and 5E illustrate cardiac CT imaging in a patient with a prior anterior myocardial infarction. Left ventricular thrombus (LVT) is noted in the apex and apical inferior wall with arrows.
Figure 5B:
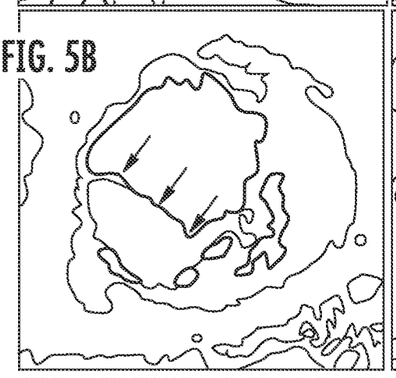
Figure 5C:
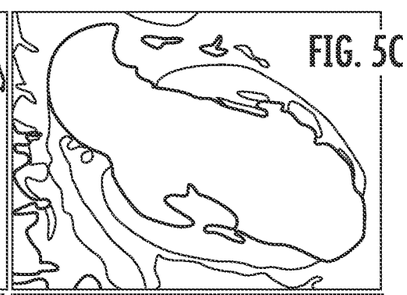
FIGS. 5C, 5D, and 5F illustrate a virtual resection of the LVT for the purposes of CFD modeling.
Figure 5D:
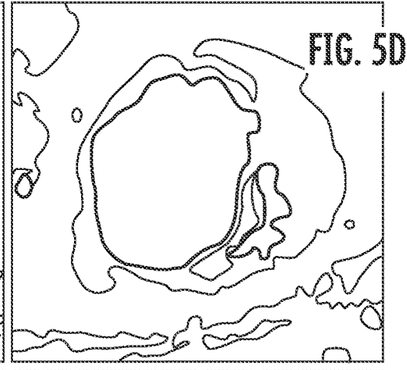
Figure 5E:
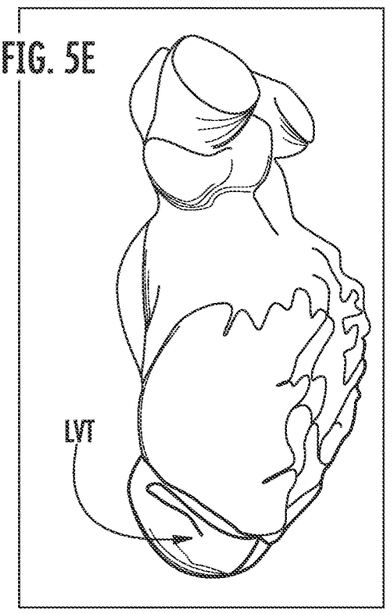
Figure 5F:
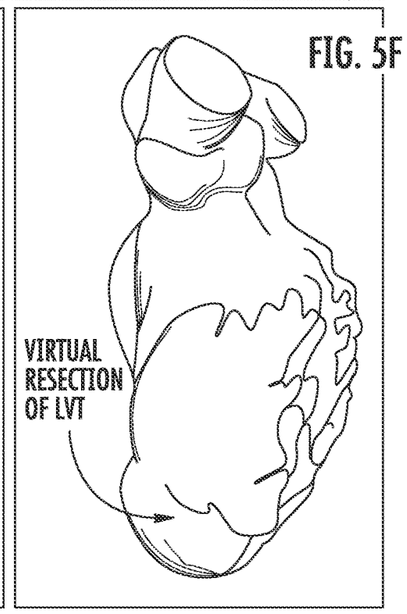

In the exemplary implementation, the generation of CFD-ready models from functional CT imaging is done using the steps associated with the method described with respect to FIG. 2. By way of example, dynamic CT Image segmentation and virtual LVT resection can be done. The LV endocardium is segmented using the software MIMICS™ at ~20 individual phases over one cardiac cycle. In cases with existing LV thrombus, the boundaries of the thrombus are carefully identified by a practitioner, as illustrated in FIG. 3 and the thrombus "virtually resected" from the endocardial boundary to generate a model that represents the pre-thrombus LV. FIG. 4 also illustrates segmentation of the CT image, according to the present invention. FIGS. 5A, 5B and 5E illustrate cardiac CT imaging in a patient with a prior anterior myocardial infarction. LVT is noted in the apex and apical inferior with arrows. FIGS. 5C, 5D, and 5F illustrate a virtual resection of the LVT for the purposes of CFD modeling. FIGS. 5E and 5F further illustrate the typical segmentation of the LV that will be employed.

Figure 6A:
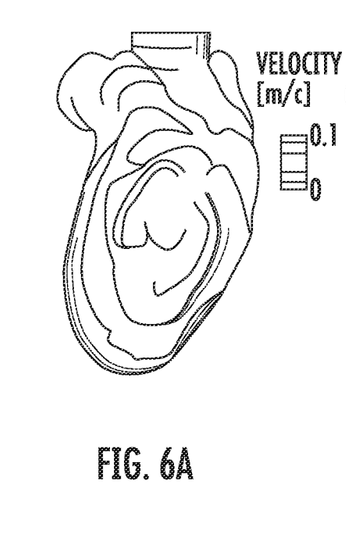
FIGS. 6A-6C illustrate CFD simulation of ventricular flow using ViCar3D, according to an embodiment of the present invention.
Figure 6B:
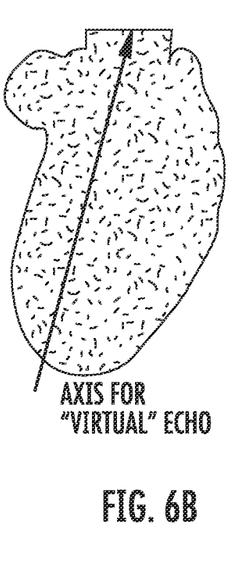
Figure 6C:
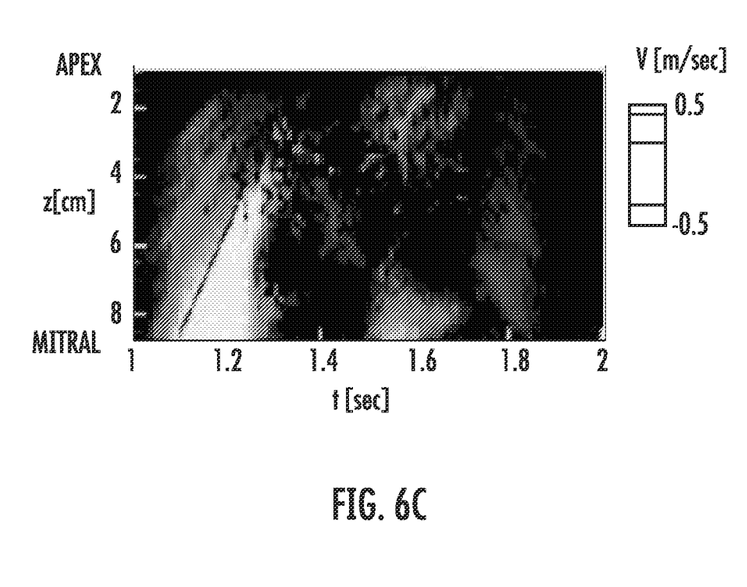

A generic template of the LV is created and shape morphing is used to register the template to each of the ~20 key-frames. This procedure ensures conformity of the geometric model across all the key frames and eliminates any artifacts due to data-gaps in the CT imaging. A space time interpolation is performed to translate the registered key-frames to $O(10^3)$ frames needed for the CFD calculation. Diastolic mitral valve leaflet motion from the CT imaging is used to fit a mitral valve model with prescribed motion in each model, as illustrated in FIGS. 6A, 6B, and 6C.

In the exemplary implementation, CFD modeling of LV hemodynamics employs an immersed boundary solver ViCar3D, for CFD modeling of complex biological flow. FIGS. 6A-6C illustrate simulation of ventricular flow using ViCar3D. FIG. 6A illustrates stream traces by velocity. FIG. 6B illustrates tracking of blood particles, and FIG. 6C illustrates M-Mode Doppler analysis of CFD data. The simulations include a Lagrangian particle tracking routine that generates many of the metrics associated with thrombogenic risk and also enables virtual echocardiography. ViCar3D provides rapid throughput on large-scale parallel computers. FIGS. 6A-6C also illustrates the simulation of early filling in a realistic left ventricle model computed using our modeling software.

Validation and verification can be carried out by modeling select cases with different grids and time-step resolutions and confirming expected convergence. The CFD data is post-processed to enable direct comparison with echocardiographic measurements, as illustrated in FIG. 6B. CT data is spatially oriented to match the orientation of the echocardiographic images using readily available landmarks such as the mitral valve leaflets, papillary muscles, RV insertion points, and trabeculae, etc. An example is the comparison of blood flow velocity along the anterior and septal walls and the LV centerline using pulse wave and color Doppler data.

The methods described herein can also be used to compute CFD-based metrics and correlate to the absence/presence of thrombus as well as thrombus location. LVT formation following acute MI is initiated by platelet deposition on the damaged akinetic/dyskinetic endocardial surface and the presence of LVT is related to the site/size of infarction and the presence of pump failure. Global or regional stagnation of blood and extent of endocardial injury may promote the development of LVT. The methods for CFD based risk stratification described herein extract a variety of hemodynamic metrics that incorporate many of the pathways implicated in LVT formation. Most of these metrics (except wall shear stress) are computed by releasing up to $10^5$ massless particles, as illustrated in FIG. 6B inside the LV model at the beginning of diastole and tracking their motion over multiple continuous cardiac cycles. Additional metrics may be also be computed by including in the CFD model, the capability to model the biochemistry associated with platelet activation and the coagulation cascade. The metrics to be computed include:

1) Particle-Residence Time (PRT): This is a measure of the time that a particle resides inside the ventricle and this metric has shown promise in predicting thrombus formation in arterial aneurysms. For each LV model, a PRT map is generated; higher magnitudes of PRT indicate a higher degree of stasis and the site of highest PRT in the LV indicates the region most susceptible to thrombus formation.

2) Particle Travel Distance (PTD): While PRT provides a gross measure of the "washout" of blood from the LV, it is not sensitive to local flow stasis. For instance, a particle that is continuously circulating in the LV with a relatively high speed is not "static" but would nevertheless have a large a residence time. PTD is the total distance traveled by a resident particle and a low PTD should indicate a region of blood stasis.

Figure 7:
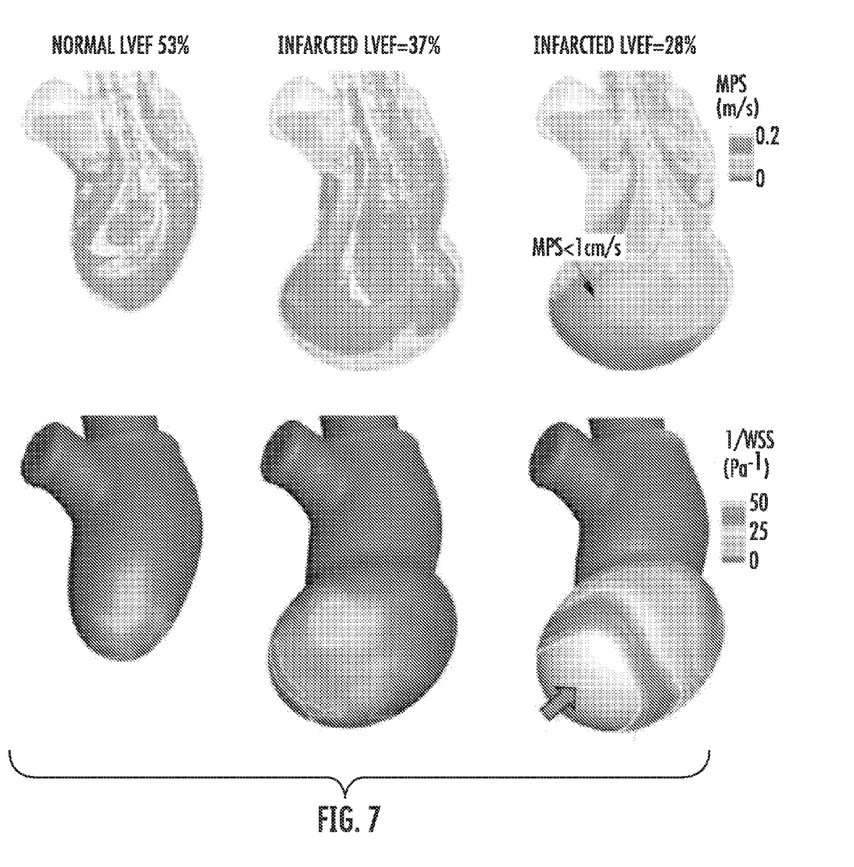
FIG. 7 illustrates metric computation for a simple LV model, according to an embodiment of the present invention.

3) Mean Particle Speed (MPS=PTD/PRT): The ratio of PTD to PRT quantifies the overall speed of a particle inside the LV and a low value of MPS implies sluggish flow and should correlate with higher thrombogenic risk. FIG. 7 illustrates data on this metric. More particularly, in the top row of FIG. 7 is illustrated MPS based thresholding of LVT risk; contours of MPS on the long-axis plane and iso-surfaces of low MPS (<1 cm/sec) region. It should be noted that a low MPS can indicate high risk of LVT. The bottom row in FIG. 7 illustrates WSS based thresholding of LVT risk; surface contours of 1/WSS. It should also be noted that a high 1/WSS can indicate a high risk of LVT.

4) Near-Wall Particle Displacement (NWPD): The endothelium in the infarcted region is in a hypercoagulable state in the first few weeks after an acute MI, and excessive residence of platelets in the proximity of the injured endothelium encourages platelet deposition and thrombus formation. High residence time of blood particles in the proximity of the infarcted wall might therefore be a particularly good indicator for thrombogenic risk but the above three metrics do not directly account for this. Therefore, a new metric (NWPD) is defined to measure stasis in the proximity of the infarcted wall. NWPD is calculated by seeding particles near the wall of interest, and calculating the total displacement of these particles from their initial location over a cardiac cycle; high values of (1/NWPD) signify near-wall stasis.

Figure 8:
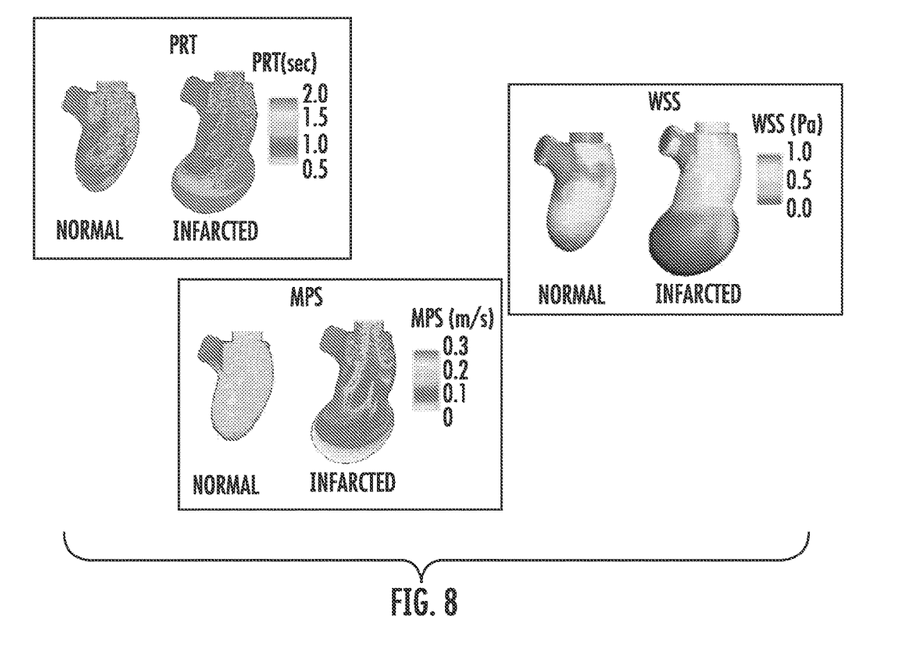
FIG. 8 illustrates preliminary CFD estimates of metrics, according to an embodiment of the present invention.

5) Wall Shear Stress (WSS): While shear stress is known to play an active role in atherogenesis, in the context of LVT, low WSS is primarily a marker of low blood flow velocity relative to the endocardium. A combination of WSS with PRT improves the ability to predict thrombus formation in arterial aneurysms and we will assess this combination as a predictor for LVT risk, as illustrated in FIG. 8. FIG. 8 also illustrates estimates of PRT and MPS CFD metrics, described above.

Figure 9A:
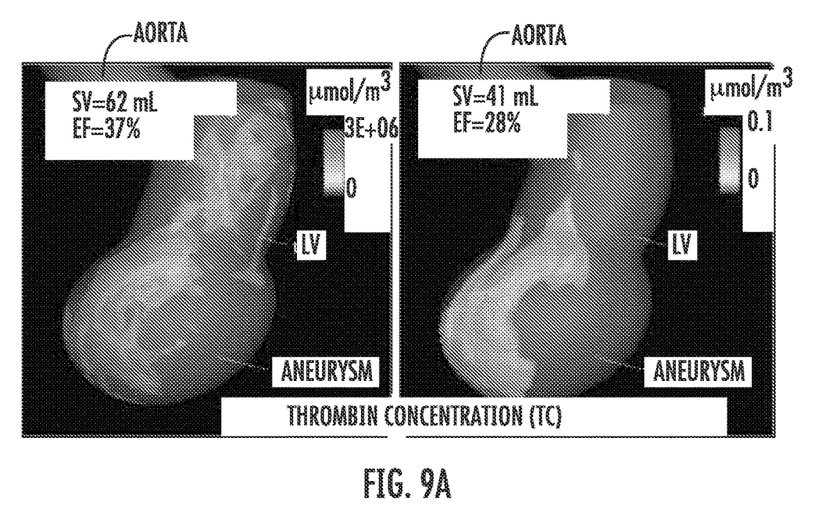
FIGS. 9A-9C illustrate CFD simulation of additional metrics, according to an embodiment of the present invention.

6) Thrombin Concentration (TC): Thrombin is a chemical that is formed in the bloodstream as part of the thombogenesis cascade and its primary function is to activate platelets. The thrombin concentration (measured in terms of micromoles per milliliter) inside the left ventricle would be computed by modeling the biochemistry of thrombin production. FIG. 9A shows results from simulations showing TC computed for a model of the left ventricle with an apical infarct.

Figure 9B:
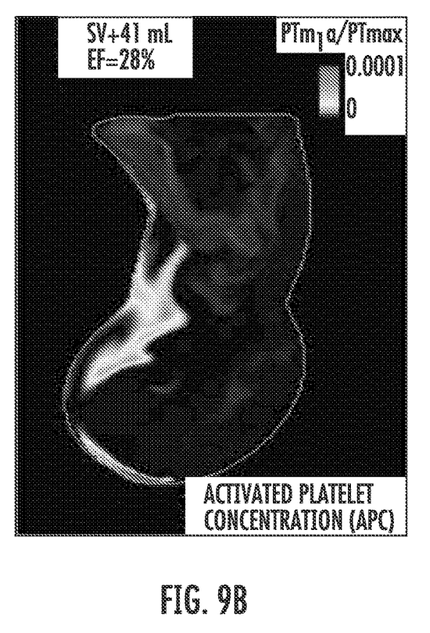

7) Activated Free Platelet Concentration (APC); Platelets get activated by thrombin; some of these platelets are free flowing in the blood while some of these get bound to the endothelium (bound platelets) to form a clot. APC would be computed by modeling this biochemistry of platelet activation. FIG. 9B shows results from simulations showing APC computed for a model of the left ventricle with an apical infarct.

Figure 9C:
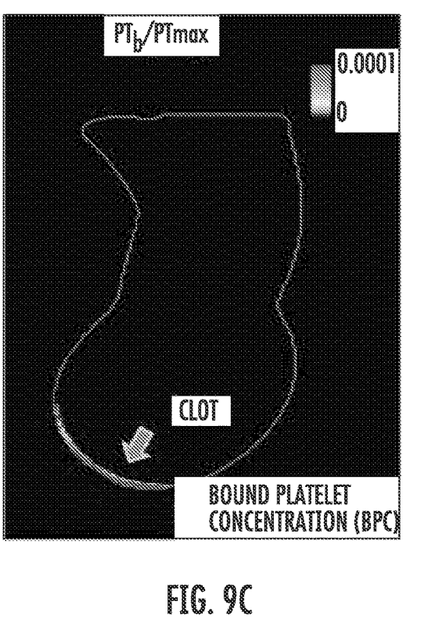

8) Bound Platelet Concentration (BPC): This would be computed by modeling the biochemistry of platelet activation and coagulation. FIG. 9C shows results from simulations showing APC computed for a model of the left ventricle with an apical infarct.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims. For instance, while the CFD approach to risk prediction described above directly addresses an important clinical problem, the risk stratification of patients for LVT, these innovations have the potential to reach a broader population at risk of cardioembolic and cryptogenic stroke significantly. Models can also be made of the left atrium and valvular structures to determine associated risk for thrombus formation.

In addition, the method can be applied to determining risk for thrombus formation in circulatory support devices including ventricular assist devices (VAD), and artificial hearts. In an application of the present invention to a patient with an VAD, the present invention can be used to determine VAD flow to minimize thrombus formation. The present invention could also be used for planning of surgery, in order to determine the most appropriate location of the VAD cannula in ventricle. Proper placement of the VAD cannula in a ventricle can help to avoid flow stasis in the patient. It should also be noted that these methods can be optimized in order to limit the effect of radiation on the patient and on the resultant image data.

The invention claimed is:

1. A method for estimating thromboembolic risk in a patient using a computing device to execute one or more steps of the method, the method comprising:
    obtaining a functional image of a heart of the patient;
    constructing a patient specific model using image data obtained from the functional image of the heart of the patient;
    modeling computational fluid dynamics (CFD) of the heart of the patient using the patient specific model to obtain fluid dynamics data from the image data;
    validating the fluid dynamics data against data obtained from an echocardiogram of the heart of the patient;
    calculating thrombogenic metrics from the fluid dynamics data; and
    generating a thrombogenic risk assessment using the metrics.

2. The method of claim 1 further comprising obtaining the functional image using at least one of a computed tomography (CT) scanner, cardiovascular magnetic resonance imager, echocardiography, and radionuclide imaging.

3. The method of claim 1 further comprising:
segmenting the functional image of the heart of the patient to obtain the patient specific model of a left ventricle of the heart;
registering a template of a generic left ventricle to the model of the left ventricle of the patient; and
simulating left ventricle flow for the model of the left ventricle.

4. The method of claim 3 further comprising segmenting the left ventricle model into 20 or more individual phases over one cardiac cycle.

5. The method of claim 4 further comprising registering the template of the generic left ventricle to each of the 20 or more individual phases.

6. The method of claim 5 further comprising performing a space-time interpolation to translate each of the 20 or more registered phases of the template frames needed for a CFD calculation.

7. The method of claim 3 further comprising identifying boundaries for a thrombus in the left ventricle model and resecting them from the model.

8. The method of claim 3 further comprising executing segmenting, registering and simulating using the computing device.

9. The method of claim 1 further comprising selecting the thrombogenic metrics from a group consisting of PRT, PTD, MPS, NWPD, WSS, TC, APC and BPC.

10. The method of claim 1 further comprising constructing the patient specific model to take the form of at least one of the atria or valvular structures.

11. The method of claim 1 further comprising selecting the thrombogenic metrics from a group consisting of TC, APC and BPC.

12. A non-transitory computer readable medium programmed with steps comprising:
receiving image data related to a functional image of a heart of a patient;
constructing a patient specific model using the image data obtained from the functional image of the heart of the patient;
modeling computational fluid dynamics (CFD) of the heart of the patient using the patient specific model to obtain fluid dynamics data from the image data;
validating the fluid dynamics data against data obtained from an echocardiogram of the heart of the patient;
calculating thrombogenic metrics from the fluid dynamics data; and
generating a thrombogenic risk assessment using the metrics.

13. The non-transitory computer readable medium of claim 12, wherein the non-transitory computer readable medium is configured for obtaining the functional image using at least one of a computed tomography (CT) scanner, cardiovascular magnetic resonance imager, echocardiography, and radionuclide imaging.

14. The non-transitory computer readable medium of claim 12 further programmed to execute steps comprising:
segmenting the functional image of the heart of the patient to obtain the patient specific model of a left ventricle of the heart;
registering a template of a generic left ventricle to the model of the left ventricle of the patient; and
simulating left ventricle flow for the model of the left ventricle.

15. The non-transitory computer readable medium of claim 14 further programmed with a step comprising segmenting the left ventricle model into 20 or more individual phases over one cardiac cycle.

16. The non-transitory computer readable medium of claim 15 further programmed with a step comprising registering the template of the generic left ventricle to each of the 20 or more individual phases.

17. The non-transitory computer readable medium of claim 16 further programmed with a step comprising performing a space-time interpolation to translate each of the 20 or more registered phases of the template to frames needed for a CFD calculation.

18. The non-transitory computer readable medium of claim 14 further programmed with a step comprising identifying boundaries for a thrombus in the left ventricle model and resecting them from the model.

19. The non-transitory computer readable medium of claim 12 further programmed to with a step comprising selecting the thrombogenic metrics from a group consisting of PRT, PTD, MPS, NW PD, WSS, TC, APC and BPC.

20. The non-transitory computer readable medium of claim 12 further programmed with a step comprising constructing the patient specific model to take the form of at least one of the atria or valvular structures.

* * * * *